US006509168B2

(12) United States Patent
Croteau et al.

(10) Patent No.: US 6,509,168 B2
(45) Date of Patent: *Jan. 21, 2003

(54) METHOD FOR QUANTIFICATION OF BIOLOGICAL MATERIAL IN A SAMPLE

(75) Inventors: Andrew J. Croteau, Peabody, MA (US); Mark W. Pierson, Saco, ME (US); David E. Townsend, Scarborough, ME (US); Ali Naqui, Falmouth, ME (US)

(73) Assignee: Biocontrol Systems, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/838,590

(22) Filed: Apr. 18, 2001

(65) Prior Publication Data

US 2002/0009766 A1 Jan. 24, 2002

Related U.S. Application Data

(63) Continuation of application No. 09/277,522, filed on Mar. 26, 1999, now Pat. No. 6,287,797, which is a continuation of application No. 08/746,054, filed on Nov. 6, 1996, now Pat. No. 5,985,594, which is a continuation-in-part of application No. 08/606,229, filed on Feb. 23, 1996, now Pat. No. 5,700,655, which is a continuation-in-part of application No. 08/557,529, filed on Nov. 14, 1995, now abandoned.

(51) Int. Cl.⁷ .............................................. C12Q 1/24
(52) U.S. Cl. .............................. 435/30; 435/4; 435/29
(58) Field of Search .............................. 435/4, 29, 30, 435/283.1, 287.1, 288.3

(56) References Cited

U.S. PATENT DOCUMENTS

| | | | |
|---|---|---|---|
| 2,771,398 A | 11/1956 | Snyder | 195/103.5 |
| 3,206,317 A | 9/1965 | Golber | 99/192 |
| 3,356,462 A | 12/1967 | Cooke et al. | 23/292 |
| 3,496,066 A | 2/1970 | Berger et al. | 195/103.5 |
| 3,649,464 A | 3/1972 | Freeman | 435/305.2 |
| 3,787,290 A | 1/1974 | Kaye | 195/103.5 R |
| 3,870,601 A | 3/1975 | Warren et al. | 195/103.5 R |
| 4,129,483 A | 12/1978 | Bochner | 195/100 |
| 4,208,480 A | 6/1980 | D'Amato et al. | 435/34 |
| 4,235,964 A | 11/1980 | Bochner | 435/34 |
| 4,240,751 A | 12/1980 | Linnecke et al. | 356/409 |
| 4,245,043 A | 1/1981 | Lund | 435/33 |
| 4,292,273 A | 9/1981 | Butz et al. | 422/102 |
| 4,315,593 A | 2/1982 | Matte | 233/21 |
| 4,495,289 A | 1/1985 | Lyman et al. | 435/284 |
| 4,545,958 A | 10/1985 | Dopatka | 422/102 |
| 4,560,535 A | 12/1985 | Bouchee | 422/102 |
| 4,591,554 A | 5/1986 | Koumura et al. | 435/18 |
| 4,622,297 A | 11/1986 | Kappner et al. | 435/32 |
| 4,675,289 A | 6/1987 | Kanou | 435/18 |
| 4,735,778 A | 4/1988 | Maruyama et al. | 422/102 |
| 4,741,619 A | 5/1988 | Humphries et al. | 356/246 |
| 4,761,378 A | 8/1988 | Godsey | 435/293 |
| 4,803,162 A | 2/1989 | Smith et al. | 435/36 |
| 4,812,409 A | 3/1989 | Babb et al. | 435/7 |
| 4,925,789 A | 5/1990 | Edberg | 435/38 |
| 5,004,684 A | 4/1991 | Simpson et al. | 435/8 |
| 5,292,644 A | 3/1994 | Berg | 435/29 |
| 5,393,662 A | 2/1995 | Roth et al. | 435/38 |
| 5,429,933 A | 7/1995 | Edberg | 435/34 |
| 5,508,005 A | 4/1996 | Mathus | 422/102 |
| 5,518,892 A | 5/1996 | Naqui et al. | 435/29 |
| 5,540,891 A | 7/1996 | Portmann et al. | 422/102 |
| 5,700,655 A | * 12/1997 | Croteau et al. | 435/30 |
| 5,985,594 A | * 11/1999 | Croteau et al. | 435/30 |
| 6,287,797 B1 | * 9/2001 | Croteau et al. | 435/30 |

FOREIGN PATENT DOCUMENTS

| | | |
|---|---|---|
| DE | 34 19327 A1 | 5/1984 |
| EP | 25 467 B1 | 3/1981 |
| EP | 59 645 B1 | 9/1982 |
| EP | 305 900 A2 | 3/1989 |
| EP | 332 752 A1 | 9/1989 |
| EP | 542 422 A1 | 5/1993 |
| GB | 2 005 410 A | 4/1979 |
| GB | 2 015 729 A | 9/1979 |
| WO | WO 91/09970 | 7/1991 |
| WO | WO 95/23026 | 8/1995 |

OTHER PUBLICATIONS

Bacteriological Ambient Water Quality Criteria for Marine and Fresh Recreational Waters, Ambient Water Quality Criteria for Bacteria, USEPA (1986).

Brenner et al., "New Medium for the Simultaneous Detection of Total Coliforms and *Escherichia coli* in Water," Applied and Environmental Microbiology 59:3534–3544 (1993).

Cabelli et al, "A Marine Recreational Water Quality Criterion Consistent with Indicator Concepts and Risk Analysis," Journal WPCF 55:1306–1314 (1983).

Cabelli, "Swimming–Associated Illness and Recreational Water Quality Criteria," *Water Sci. Tech.* 21: 13–21, 1989.

Dahlen and Linde, "Screening Plate Method for Detection of Bacterial β–Glucuronidase," *Applied Microbiology* 26: 863–866, 1973.

(List continued on next page.)

Primary Examiner—Dameron L. Jones
(74) Attorney, Agent, or Firm—Seed Intellectual Property Law Group PLLC (57) ABSTRACT

Method for detection of a biological material in a sample. The method includes the steps of liquifying the sample (if necessary) and pouring the liquified sample into the incubation plate. The incubation plate has a generally flat horizontal surface and the surface is divided into a plurality of at least 20 recessed wells. Each well is adapted to hold an aliquot of liquid and is sized and shaped, and formed of a suitable material, to hold the aliquot within the well by surface tension. Any excess liquid from the liquified sample is poured from the surface of the plate. The method then involves incubating that incubation plate until the presence or absence of the biological material is determined.

20 Claims, 5 Drawing Sheets

OTHER PUBLICATIONS

Damare et al., "Simplified Direct Plating Method for Enhanced Recovery of *Escherichia coli* on Food," *J. Food Science 50*: 1736–1738, 1985.

de Man, "The Probability of Most Probable Numbers," European J. Appl. Microbiol. 1:67–78 (1975).

Donnelly and Hartman, "Gentamicin–Based Medium for the Isolation of Group D Streptococci and Application of the Medium to Water Analysis," Applied And Environmental Microbiology 35:576–581 (1978).

Gatti and Neviani, "A New Simple Medium for the Detection of Enterococcus Faecalis and Enterococcus Faecium by Measurement of Conductance Changes," Letters in Applied Microbiology 17:72–74 (1993).

Hansen and Yourassowsky, "Detection $\beta$–Glucuronidase in Lactose–Fermenting Members of the Family Enterobacteriaceae and Its Presence in Bacterial Urine Cultures," J. Biol. Chem. 20:1177–1179 (1984).

Hernandez et al., "MPN Miniaturized Procedure for the Enumeration of Faecal Enterococci in Fresh and Marine Waters: The Must Procedure," Wat. Res. 27:597–606 (1993).

Jay (ed.), *Modern Food Microbiology*, 4th ed., Van Nostrand Reinhold, New York, 1992, Chapter 5, "Culture, Microscopic, and Sampling Methods," pp. 113–121.

Kendall et al., "Observations of the Relative Constancy of Ammonia Production by Certain Bacteria," J. Infectious Diseases 13:425–428 (1913).

Kilian and Bölow, "Rapid Identification of Enterobacteriaceae," Acta Path. Microbiol. Scand. Section B 87:271–276 (1979).

Knudtson and Hartman, "Comparison of Fluorescent Gentamicin–Thallous–Carbonate and KF Streptococcal Agars to Enumerate Enterococci and Fecal Streptococci in Meats," Applied and Environmental Microbiology 59:936–938 (1993).

Littel and Hartman, "Fluorogenic Selective and Differential Medium for Isolation of Fecal Streptococci," Applied and Environmental Microbiology 45:622–627 (1983).

Maddocks and Greenan, "Technical Method: A Rapid Method for Identifying Bacterial Enzymes," J. Clinical Pathology 28:686–687 (1975).

Mooney et al., Testing the Waters: A National Perspective on Beach Closings, Natural Resources Defense Council, pp. 1–67 (1992).

Peeler et al., *Compendium of Methods for the Microbiological Examination of Foods,* Amercian Public Health Association, Washington, DC, 1992, Chapter 6, "The Most Probable Number Technique," pp. 105–120.

Sarhan and Foster, "A Rapid Fluorogenic Method for the Detection of *Escherichia coli* by the Production of $\beta$–glucuronidase," J. Applied Bacteriology 70:394–400 (1991).

Standard Methods for the Examination of Water and Waste Water, 18th ed., American Public Health Association, Washington, DC, 1992, Greenberg et al. eds., pp. 9–69 to 9–73.

Standard Methods for the Examination of Water and Waste Water, 18th ed., American Public Health Association, Washington, DC, 1992, Greenberg et al. eds, pp. 9–45 to 9–64.

Thomas, "Bacterial Densities From Fermentation Tube Tests," J. Am. Water Works Assoc. 34:572–576 (1942).

Trepta and Edberg, "Esculinase ($\beta$–glucosidase) for the rapid estimation of activity in bacteria utilizing a hydrolyzable substrate, p–nitrophenyl–$\beta$–D–glucopyranoside," Antonie van Leeuwenhoek 53:273–277 (1987).

Trepeta and Edberg, "Methylumbelliferyl–$\beta$–D–Glucuronide–Based Medium for Rapid Isolation and Identification of *Escherichia coli*," J. Clinical Microbiology 19:172–174 (1984).

Ur and Brown, "Impedance Monitoring of Bacterial Activity," J. Med. Microbiol. 8:19–28 (1975).

* cited by examiner

METHOD FOR QUANTIFICATION OF BIOLOGICAL MATERIAL IN A SAMPLE

CROSS-REFERENCE TO RELATED APPLICATION

This Application is a continuation of U.S. Ser. No. 09/277,522, filed Mar. 26, 1999 and now U.S. Pat. No. 6,287,797; which application is a continuation of U.S. Ser. No. 08/746,054, filed Nov. 6, 1996, which issued as U.S. Pat. No. 5,985,594 on Nov. 16, 1999; which application is a continuation-in-part of Croteau et al., U.S. Ser. No. 08/606,229 filed Feb. 23, 1996, now U.S. Pat. No. 5,700,655, issued Dec. 23, 1997 which is a continuation-in-part of Croteau et al., U.S. Ser. No. 08/557,529, filed Nov. 14, 1995, now abandoned, both entitled "Method for Quantification of Biological Material in a Sample" hereby incorporated herein by reference, including drawings.

FIELD OF THE INVENTION

This invention relates to a method for quantification of biological material in a sample.

BACKGROUND OF THE INVENTION

Many industries need to detect and quantify the concentration and level of biological material in a sample. For example, the determination of bacterial concentration in food and water is an essential part of food and water quality testing. EPA regulations require that no Coliform such as *Escherichia coli* can be present in potable water. The "presence/absence" format of a testing medium, such as Colilert® chemical mixture (IDEXX Laboratories, ME) which is used as a testing medium for *Escherichia coli* and all coliform bacteria, is very useful in making this determination. Colilert® chemical mixture is based on the Defined Substrate Technology described in Edberg, "Method and Medium for use in Detecting Target Microbes In Situ in A Specimen Sample of A Possibly Contaminated Material," U.S. Pat. Nos. 4,925,789 and 5,492,933. See also, Townsend et al., U.S. Ser. No. 08/484,593 filed Jun. 7, 1995 entitled, "Method and Composition for Detecting Bacterial Contamination in Food Products", hereby incorporated by reference herein, describes a medium for the detection of bacteria in food and water samples.

However, there are areas where the quantification, not just the detection, of bacterial concentration is important. Examples of such areas include waste water, incoming water in water purification systems, surface water, and food testing. For example, numerous restaurant chains will only accept raw ground beef or poultry that contains less than a certain concentration of bacterial contamination. Therefore, food processing plants must carry out the necessary microbiological tests to determine the bacterial concentration of these food items before they can be released to customers.

The classical methods of quantification of biological material are the standard plate count method or the multiple tube fermentation (MTF) method. A quantity of sample being tested for microbial contamination is first dispensed in a Petri dish. Then 15 ml of the appropriate media is poured over the sample. The Petri-dish is then swirled to mix the sample in the medium and the Petri-dish is left to solidify at room temperature for approximately 20 minutes. The medium is then incubated at a specific temperature for a specific time, and any resulting colonies are counted.

The multiple tube fermentation method is described in Recles et al., "Most Probable Number Techniques" published in "Compendium of Methods for the Microbiological Examination of Foods", 3rd ed. 1992, at pages 105–199, and in Greenberg et al., "Standard Methods For the Examination of Water and Wastewater" 8th ed. 1992). In this method, a volume of sample is dispensed into several tubes representing this dilution range. The tubes are then incubated at the appropriate temperature so that the bacteria in each tube are allowed to grow. After incubation at a specific temperature for a specific time, the number of positive tubes is counted. The most probable number can be determined from the formula described in Recles et al., supra.

Water testing is mostly done by membrane filtration, where a certain volume of water is passed through the membrane and the membrane is incubated in a medium for a certain period of time. After appropriate incubation, the colonies are counted.

SUMMARY OF THE INVENTION

The present invention provides a simple method for more accurate quantification of the number of microorganism in a sample, or for quantification of any other type of discrete particulate biological material within a sample. Such biological materials include fungi or other living organisms, as well as aggregates of proteins, such as enzymes, or even co-factors, using reaction mixtures well known to those in the art. The invention generally makes use of a novel article which is designed to hold a liquid sample in which chemical and/or microbiological reactants are provided. For example, such chemical reactants may be a specific growth medium for bacteria. The device used is generally in the form of an incubation plate having a multitude of wells able to hold separate aliquots of liquid. Generally, the device is designed to hold between 5 and 100 ml of liquid in total, and the wells are designed to form separate incubation chambers for each aliquot of sample. The wells can be of same size or of different size and shape to increase counting range and/or simulate dilution effects. See, Naqui et al., U.S. Ser. No. 08/201,110, filed Feb. 23, 1994, entitled "Apparatus and Method for Quantification of Biological Material in a Liquid Sample", incorporated by reference herein.

Figure 3:
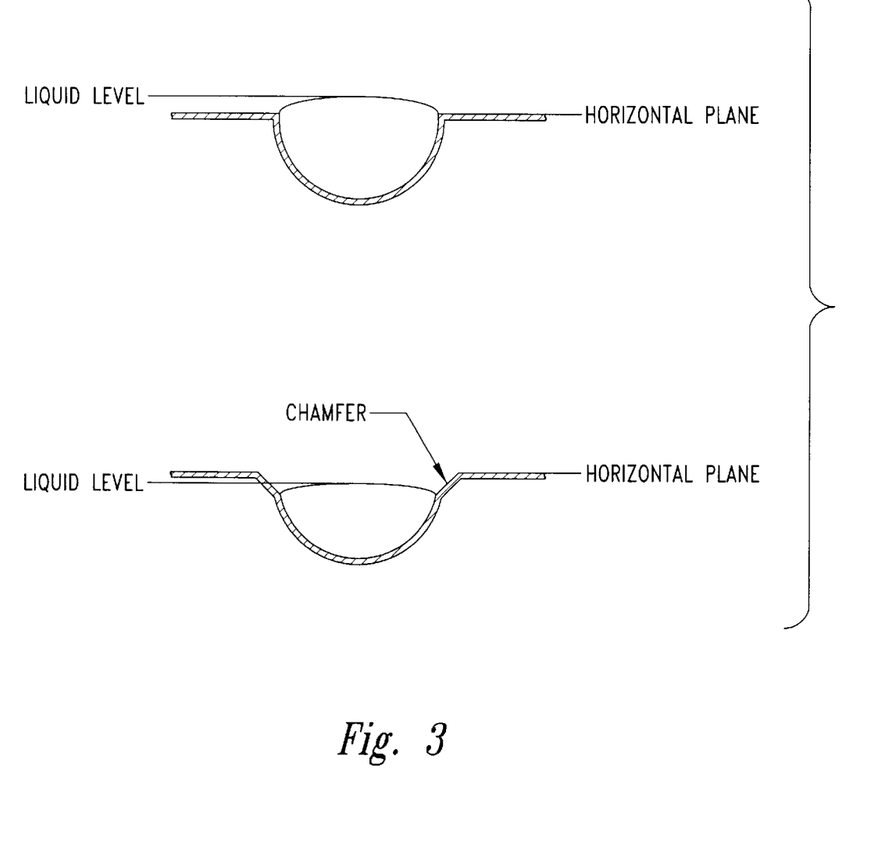
FIG. 3 shows a cross section of a well, with or without a chamfer.

Thus, in a first aspect the invention features a method for detection of a biological material in a sample. The method includes the steps of liquifying the sample (if necessary) and pouring the liquified sample and reagent into the incubation plate. The incubation plate has a generally flat horizontal surface and the surface is divided into a plurality of at least 20 recessed wells. Each well is adapted to hold an aliquot of liquid and is sized and shaped, and formed of a suitable material, to hold the aliquot within the well by surface tension. Any excess liquid from the liquified sample is poured from the surface of the plate due to the hydrophobicity of the material used to form the plate. The method then involves incubating that incubation plate until the presence or absence of the biological material is determined. In a preferred embodiments the wells are chamfered to allow liquid, that is above the horizontal plane, to be poured off easily (see FIG. 3).

As noted above, the biological material that can be detected is any material that forms a discrete particle, such as a microorganism, which may be quantified by determining the presence or absence of such a biological material within each well of the incubation plate. The sample may be any biological sample or environmental sample such as waste water, food, a surface swab, or swabs from other surfaces, such as a throat, or other samples well known to those in the art. This sample may be a liquid sample, or may be dissolved in a liquid to form the liquified sample. Thus, the term "liquifying" in the above paragraph refers to providing the sample in a liquid that once combined with a microbiological reagent can be rapidly aliquoted within the incubation plate. The liquidified sample may remain as a liquid or may be solidified in the wells.

The incubation plate may be formed of any desired material, but in particular it is desirable that a plastic be used which allows separate aliquots of the liquified sample to be held by surface tension within each well without cross contamination of the wells. Preferably, the material is hydrophobic. The surface can be untreated or treated chemically or physically to enhance retention of liquid witning the wells.

The shape of the incubation plate is not relevant, and in preferred embodiments is a generally circular shape (such as that of a Petri dish). Indeed, the incubation plate can be used to take the place of a Petri dish. Specifically, the method of this invention can be used to replace those existing tests that are generally run on Petri dishes to score the number of bacterial colonies. Since discrete aliquots of the sample are provided in the plate, one of ordinary skill in the art need only score the number of positive wells in the plate to define the quantity of biological material within the original sample, as with the MPN test discussed above.

The generally flat horizontal surface is designed to allow the liquid to be aliquoted readily between the wells and then excess liquid to be poured from the plate. In a preferred embodiment, a lip or pouring spout is provided for the plate. Those in the art will recognize that the depth and shape of the wells, as well as the material used to make the wells and the plate, are chosen such that surface tension can be used to hold the aliquots within each well dependent on the type of the liquid used in the liquified sample.

In other preferred embodiments, the surface defines at least 40, 60, 80 or even 200 or more recessed wells; the plate is formed of any formable plastic; a lid is also provided to prevent contamination of liquid within the wells; and the plate is provided in a sterile form so that no positive aliquots are noted unless at least one biological material particle is present in the sample.

In yet other preferred embodiments, the incubation plate is clear or colored, for example, white or yellow (to enhance the appearance of color (e.g., blue)) within the incubation plate) and the well has a diameter of about 0.15 inches, and the plate a diameter of about 3 or 5 inches.

In still other preferred embodiments, the incubation plate has a "pour-off pocket" adjacent to the surface of the plate. The pocket has sufficient capacity to contain the excess liquid to be removed from the plate surface. As an aid in preventing the excess fluid from spilling back onto the plate surface, it is preferable that the pocket contain an absorbent material, e.g., a gauze-like material. In a particular embodiment, the plate has both a pour-off pocket and a "landing pad". The "landing pad" is described below.

In a related aspect, the invention features a sterile incubation plate having a generally flat horizontal surface. The surface defines a plurality of at least 20 recessed wells (in preferred embodiments, at least 40, 60, 90 or even 200 recessed wells are provided) and each well is adapted as described above to hold aliquots of liquid by surface tension.

In preferred embodiments, the invention features the sterile incubation plate much as described above but having incorporated therein a "landing pad", which is a generally central area of the plate lacking wells, which can receive the sample prior to that sample being diluted in, for example, an incubation medium. Thus, a volume of 0.01 to 5 ml of sample liquid maybe applied in the "landing pad" area (depending on its size and shape) and then that liquid dispensed into each well by applying the diluent and growth supporting medium (e.g., the Colilert™ chemical mixtures noted above) and that liquid will simultaneously dilute the sample and allow dispersion of the sample throughout the wells.

In addition, a pour spout can be provided within the incubation plate to allow pouring off excess liquid within the plate. Such a pour spout can be matched with a suitable lid having a slit which allows liquid in the incubation plate to be poured from the incubation plate only when the slit is lined up with the pour spout, as described below.

As indicated for the method above, the incubation plate may also have a "pour-off pocket" adjacent to the surface of the plate. The pocket has sufficient capacity to contain the excess liquid to be removed from the plate surface, and preferably the pocket contains an absorbent material, e.g., a gauze-like material. In a particular embodiment, the plate has both a "pour-off pocket" and a "landing pad".

Applicant provides an extremely useful method which allows unskilled personnel to rapidly determine the quantity of biological material within a sample. Since the sample is readily liquified by people without significant training in microbiology, and the materials for any specific tests can be provided by the manufacturer, such people can readily perform the tests with accuracy. The incubation plate is generally provided in the sterile form so that no inappropriate detection of biological material can occur.

While it is known to provide plastic containers which can hold liquid within a plurality of recesses, applicant believes that this device provides a new automatic aliquoting method. This is an improvement over the existing products used to detect and quantify microorganisms because the liquid migrates to the individual wells without individual dispensing.

The present device can replace the use of a Petri dish and can be used particularly in food analysis and in testing of clinical samples. The separation of the wells of the present device prevents crosstalk or contamination between each aliquot. Because of this, many of the tests can be performed by observing fluorescence (which is not readily performed in an agar-containing Petri dish. The device is particularly useful when there is a large quantity of microorganisms present in a sample, such as more than one organism per one ml or per ten ml.

Other features and advantages of the invention will be apparent from the following description of the preferred embodiments thereof, and from the claims.

DESCRIPTION OF THE PREFERRED EMBODIMENT

The drawing will first briefly be described.

Drawings

Structure

Figure 1:
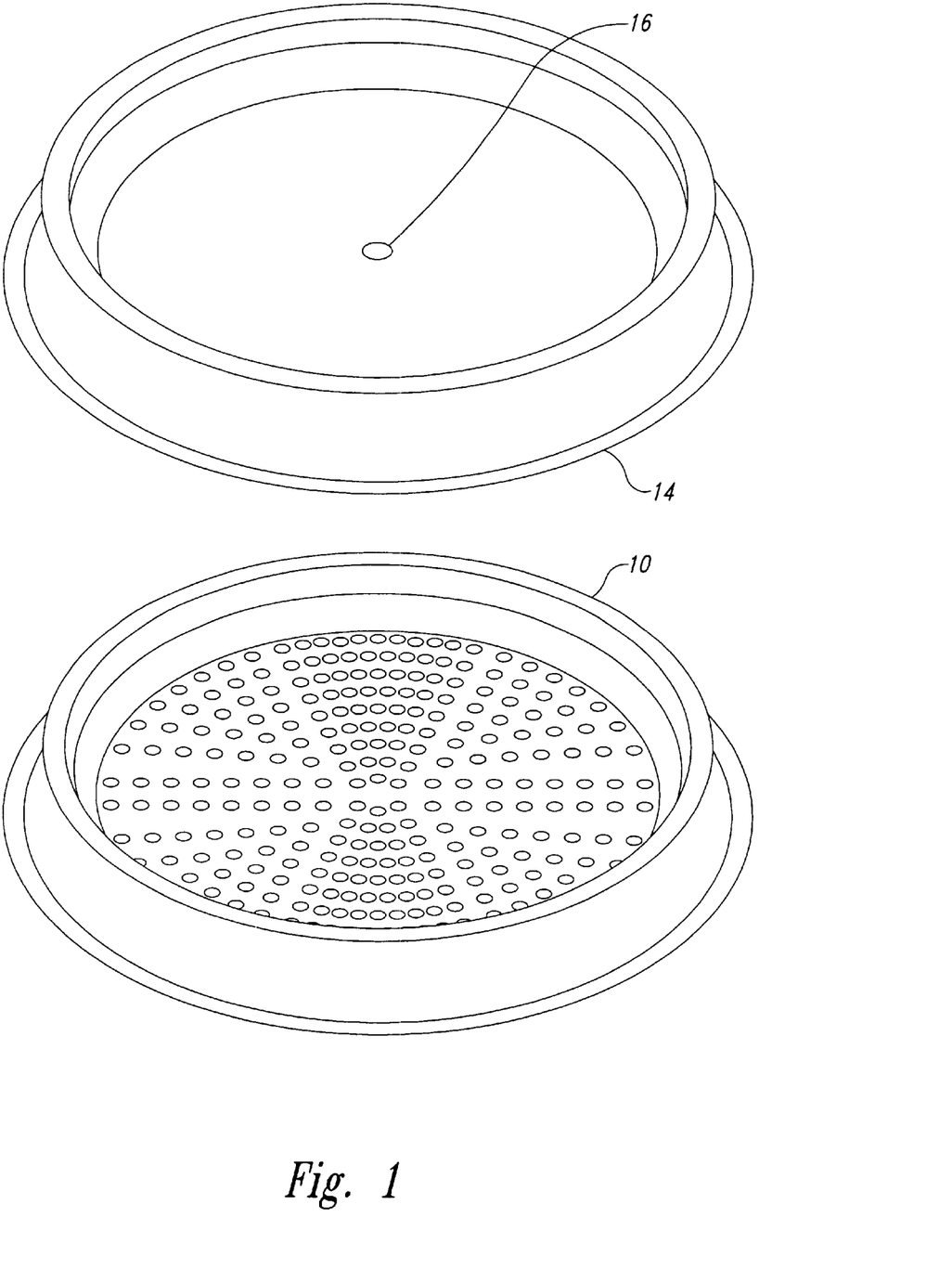
FIGS. 1 and 2 are diagrammatic representations of a formed plastic incubation plate.
Figure 2:
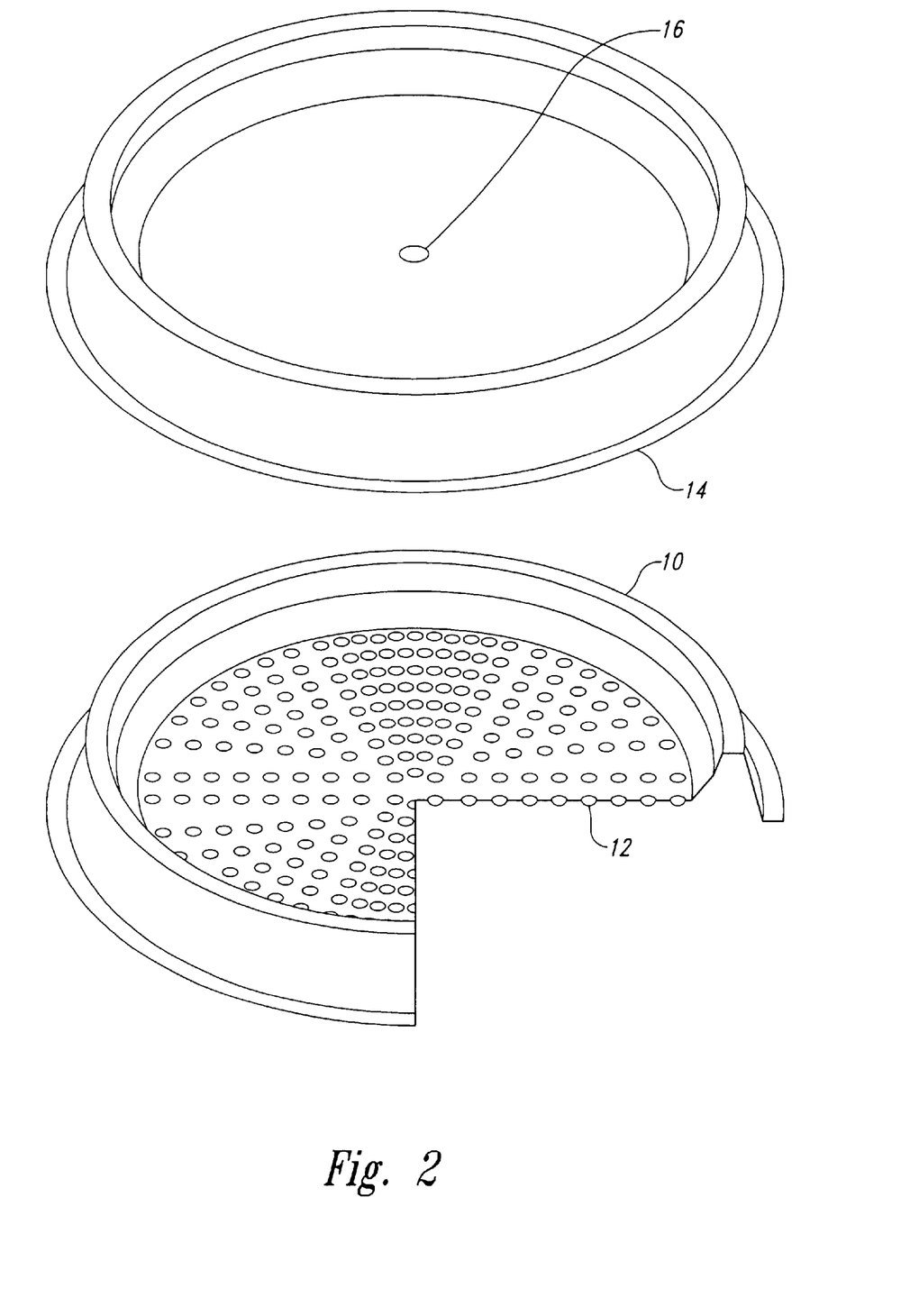

Referring to FIGS. 1 and 2 there is shown an incubation plate 10 having a plurality of wells 12 each having a diameter of about 0.16 inches. The incubation plate 10 has a diameter of about 5 inches. The incubation plate is made of formed plastic. Wells 12 are spaced apart sufficiently to prevent crosstalk between the wells. These wells may have a chamfer (FIG. 3) if desired to prevent liquid remaining at the upper edge of the well. Those in the art will recognize that incubation plate 10 can be readily formed by standard procedure and manufactured in the general shape of a Petri dish, with or without a lip or pouring spout, and with or without a lid 14. This lid is provided with a dimple 16 to prevent contact of the lid with plate 10.

Figure 4:
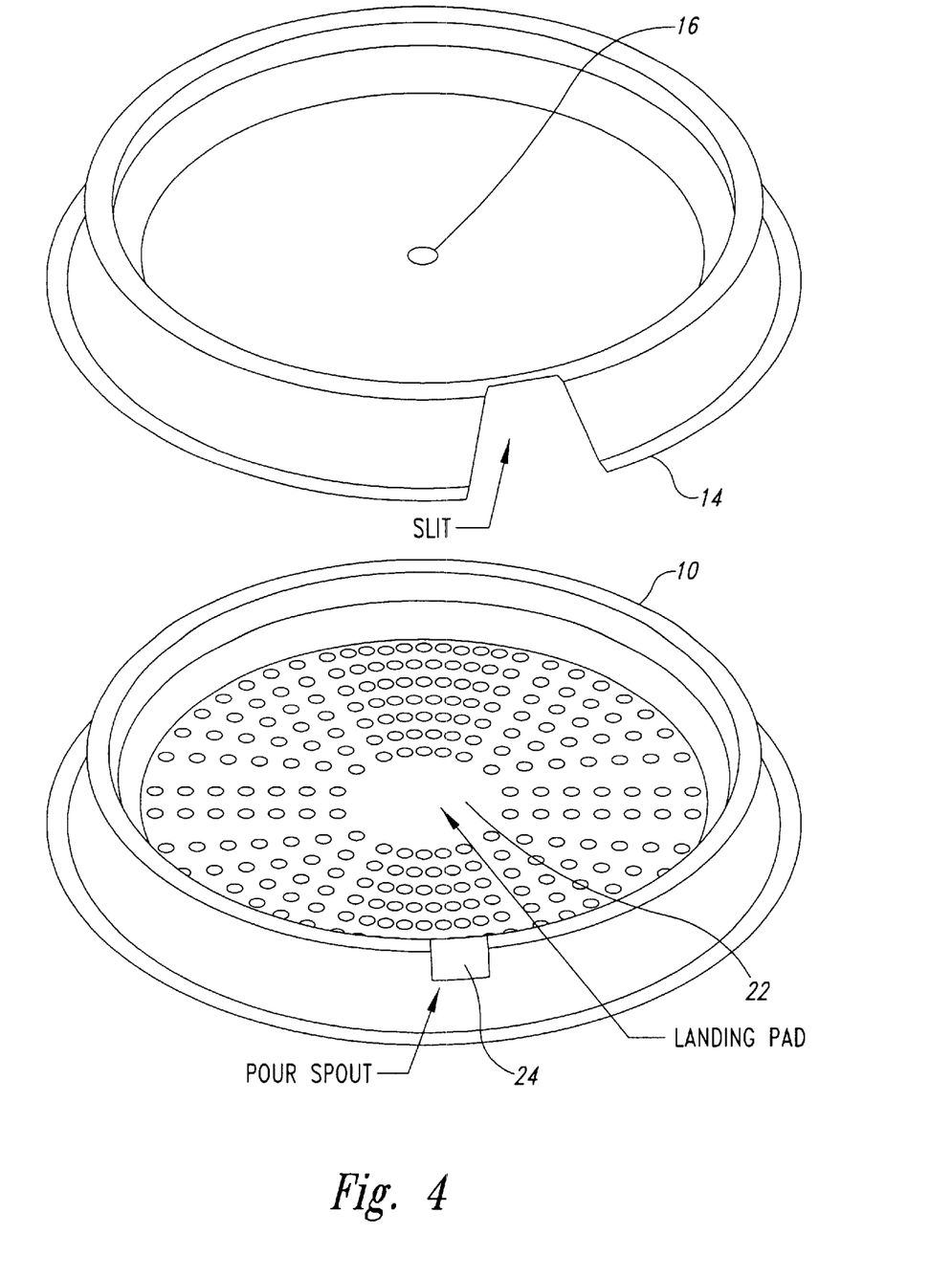
FIG. 4 is a diagrammatic representation of a formed plastic incubation plate having a pour spout and corresponding slit as well as a "landing pad".

Referring to FIG. 4, there is shown in incubation plate 10 having a plurality of wells much as described above. The incubation plate also includes a "landing pad" 22 of size about one and one-half inch diameter which is simply an area able to hold a defined volume of liquid. Within the incubation plate is also provided a pour spout 24 which allows excess liquid to be removed from the incubation plate. Also provided is a corresponding lid 14 having a slit which can be matched with the pour spout to allow liquid to be removed from the incubation plate. When the slit is not aligned with the pour spout, evaporation of liquid within the plate is decreased by reducing air flow over the liquid in the wells. A dimple 16 may also be provided in the lid to prevent the lid surface contacting the wells and thus preventing cross contamination between the wells.

Figure 5A:
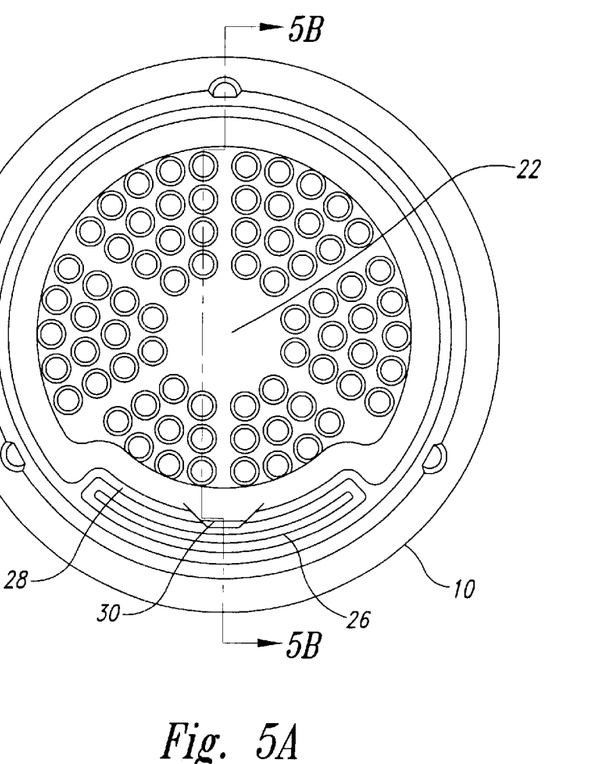
FIG. 5 is a diagrammatic representation of a formed plastic incubation plate having a "landing pad" and a "pour-off pocket".
Figure 5B:
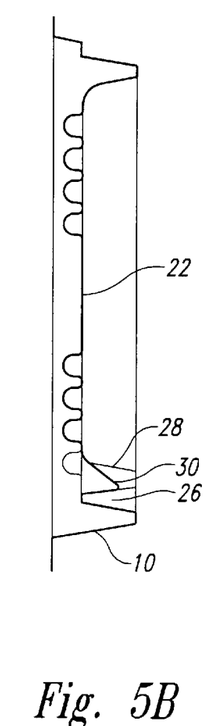

Referring to FIG. 5, there is shown an incubation plate 10 having a plurality of wells much as described above, which also includes a "landing pad" 22 of size about one inch diameter. Within the incubation plate is also provided a "pour-off pocket" 26 adjacent to the surface of the plate which allows excess liquid to be removed from the incubation plate. As shown in the cross-sectional view, the "pour-off pocket" is formed by an elevated barrier 28 between the pocket and the plate surface. The barrier has a lower barrier section 30, which serves as a channel through which the excess fluid from the plate surface may be poured into the pocket. Typically, the pocket will contain an absorbent material which will retain the fluid within the pocket, preventing back spill onto the plate surface.

Use

In use, a reagent powder suitable for detection of a biological material can be rehydrated with an appropriate amount of sterile liquid and then inoculated with a known volume of a test sample. For example, 20 ml of sterile water can be inoculated with between 10 and 1,000 microliter of sample. The inoculated reagent can then be added to incubation plate 10 and that liquid swirled within incubation plate 10 to distribute the inoculated liquid reagent to each of wells 12. Incubation plate 10 is then held at an angle of approximately 90 degrees to allow excess inoculated liquid reagent to be removed from the plate. A lid may then be placed on the incubation plate and that plate held in an incubator for the appropriate length of time, for example 18–48 hours. After that length of time, the presence or absence of a positive result can be scored in each well 12 of the plate. In adition, for plates having a "pour-off pocket", due to the larger volume of fluid contained in the pocket, a positive result in the pocket can serve as an early indication of high bacterial counts.

Example 1

Use of Incubation Plate For Bulk Testing

For total plate count a plate as described above is used for the detection and quantification of the total bacterial concentration of food. It is based on a Multiple Enzyme Technology (Townsend and Chen, Method and Composition for Detecting Bacterial Contamination in Food Products, U.S. Ser. No. 08/484,593 hereby incorporated by reference herein) which correlates enzyme activity to the presence of viable bacteria in food. It utilizes multiple enzyme substrates that produce a blue fluorescent color when metabolized by bacteria. When the liquid reagent is inoculated with a prepared food sample and dispensed into a plate, as described herein the total viable bacterial concentration of that food product can be determined after 24 hours of incubation. The actual medium used herein is not critical to the invention, but is provided only for illustrative purposes.

Storage and Disposal

Store bulk powder and unused Simplates at room temperature (4 to 25° C.) away from the light. After use, the Simplate device will contain viable bacteria which must be handled and discarded appropriately. Once the powder is rehydrated it is stable for up to 24 hours when stored at 4 to 25° C.

Test Procedure

1. Pour an appropriate amount of bulk powder to a container of sterile deionized water. One vial contains enough powder for 10 tests. Each test has a final volume of 10 ml. For example: add 1 vial of powder to 100 ml of sterile water to make enough media for 10 tests.

2. Place test sample on the center "landing pad" 22 of the plate 10 shown in FIG. 4. At the completion of this procedure half of the test sample will be poured off and discarded, therefore, the size of the inoculum must take this into account. For example, if you wish to measure the bacterial concentration of 0.1 ml of test sample then you must place 0.2 ml of test sample on the "landing pad". Place no more than 2 ml on the center "landing pad".

3. Remove the lid from the plate and dispense 10 ml of TPC media in the plate making sure to direct the liquid over the test sample on the center "landing pad". If the test sample is greater than 0.1 ml add enough TPC to achieve a final volume of 10 ml in the plate. Note, if the liquid is not dispensed on the "landing pad" it may splatter.

4. Place the lid back on the plate. Note, to ensure that the liquid remains in the Simplate make sure that the slit on the lid is not lined up with the pour spout.

5. Distribute the liquid into the wells by swirling the plate as you would a standard pour plate.

6. Line up the slit on the lid with the pour spout and carefully pour off the excess liquid that did not end up in the wells. Holding the plate at an angle of approximately 90° from the work bench ensures proper pour off of excess liquid. Make sure that all liquid "cross bridges" between wells are removed by gently tapping the plate. Dispose of excess liquid appropriately.

7. Slide the lid away from the pour spout to avoid drying the liquid in the wells during incubation and to avoid contamination from outside through the opening.

8. Place the plate in an incubator for 24 hours. Plates can be inverted if desired. Incubation temperatures greater than 37° C. are not recommended.

9. Count the number of fluorescent wells after 24 hours by placing a 6 watt 36 nm UV light within five inches of the plate. Do not read plate before 24 hours. Results are stable to 48 hours.

10. Compare the number of fluorescent wells to an MPN chart to determine the most probable number of bacterial present in the plate.

Test Procedure, Using Plate Having "Pour-Off Pocket"

1. Pour an appropriate amount of bulk powder to a container of sterile deionized water. One vial contains enough powder for 10 tests. Each test has a final volume of 10 ml. For example: add 1 vial of powder to 100 ml of sterile water to make enough media for 10 tests.

2. Place test sample on the center "landing pad" 22 of the plate 10 shown in FIG. 5. At the completion of this procedure half of the test sample will be poured off into the pocket, therefore, the size of the inoculum must take this into account. For example, if you wish to measure the bacterial concentration of 0.1 ml of test sample then you must place 0.2 ml of test sample on the "landing pad". Place no more than 2 ml on the center "landing pad".

3. Remove the lid from the plate and dispense 10 ml of media in the plate making sure to direct the liquid over the test sample on the center "landing pad". If the test sample is greater than 0.1 ml add enough media to achieve a final volume of 10 ml in the plate. Note, if the liquid is not dispensed on the "landing pad" it may splatter.

4. Distribute the liquid into the wells by swirling the plate as you would a standard pour plate, taking care that the fluid does not enter the "pour-off pocket".

5. Carefully pour off the excess liquid that did not end up in the wells through the "pour-off pocket" barrier channel. Holding the plate at an angle of approximately 90° from the work bench ensures proper pour off of excess liquid. Make sure that all liquid "cross bridges" between wells are removed by gently tapping the plate.

6. Place the plate in an incubator for 24 hours. Plates can be inverted if desired if the "pour-off" pocket contains an absorbent material.

7. Count the number of fluorescent wells after 24 hours by placing a 6 watt 36 nm TV light within five inches of the plate. Do not read plate before 24 hours. Results are stable to 48 hours.

8. Compare the number of fluorescent wells to an MPN chart to determine the most probable number of bacterial present in the plate.

Example 2

Use of Incubation Plate for Unit Dose Testing

The plate and media described in Example 1 are used for this test.

Test Procedure

1. Add 10 ml of sterile water to the tube of predispensed powder. If greater than 0.1 ml of food sample is to be inoculated into the test, reduce the volume of sterile water appropriately to achieve a final volume of 10 ml in the tube.

2. Inoculate the liquid reagent with the food sample being tested.

3. Shake tube several times to completely mix powder and inoculated food sample. Avoid excessive mixing which tends to foam up liquid reagent. Too much foam can complicate the distribution of the liquid into the plate. The rest of the procedure is as in Example 1.

Other embodiments are within the following claims.

What is claimed is:

1. An incubation plate for the determination of the amount of a biological material having a generally flat horizontal surface, said surface defining a plurality of at least twenty wells or separate incubation chambers, each which holds an aliquot of liquid and being sized and shaped, and formed of a material which holds said aliquot within each said well or separate incubation chamber wherein said aliquot is held by surface tension or by gelling said liquid or by treating the surface chemically or physically to increase retention of liquid, wherein said incubation plate will not provide any positive response for said biological material in the absence of a said biological material present in a sample applied to said plate.

2. The plate of claim 1, wherein said plate is formed of plastic.

3. The plate of claim 2, wherein said plastic is polyvinyl chloride.

4. The plate of claim 2, wherein said plastic is formed of a hydrophobic material.

5. The plate of claim 2, wherein said plate is generally circular in shape.

6. The plate of claim 1, wherein said incubation plate is provided with a lid to prevent contamination of liquid in said wells.

7. The plate of claim 2, wherein the plate is colored or clear.

8. The plate of claim 7, wherein the plate is white or yellow.

9. The plate of claim 1, wherein each said well or chamber is about 0.15 inch in diameter.

10. The plate of claim 1, wherein said plate is about three inches diameter.

11. The plate of claim 1, wherein said plate is about five inches diameter.

12. The plate of claim 1, wherein said plate has a lid to allow removal of excess liquid not held in a well from the plate.

13. The plate of claim 1, wherein said wells or said chambers hold a total of between five and 100 ml.

14. The plate of claim 1, further comprising a pour-off pocket adjacent to said surface of said plate, wherein said pocket contains excess liquid removed from said surface of said plate.

15. The plate of claim 1, wherein said plate comprises a landing pad which holds a sample prior to aliquoting of said sample to said wells.

16. The plate of claim 1, wherein said plate comprises a pour spout.

17. The plate of claim 16, wherein said plate further comprises a lid having a slit which cooperates with said pour spout to allow removal of liquid said incubation plate.

18. The plate of claim 15, further comprising a pour-off pocket adjacent to said surface of said plate, wherein said pocket contains excess liquid removed from said surface of said plate.

19. The plate of claim 18, further comprising an absorbent material within said pour-off pocket.

20. The plate of claim 1, wherein said plate is sterile.

* * * * *